United States Patent [19]

Yen

[11] 4,053,477

[45] Oct. 11, 1977

[54] 5-(1,1-DIPHENYL-3-(4-PHENYL-PIPERIDINO)PROPYL)-2-METHYL-1,3,4-OXADIAZOLE AND RELATED COMPOUNDS

[75] Inventor: Chung H. Yen, Skokie, Ill.

[73] Assignee: G. D. Searle & Co., Chicago, Ill.

[21] Appl. No.: 724,790

[22] Filed: Sept. 20, 1976

[51] Int. Cl.$^2$ .......................................... C07D 413/10
[52] U.S. Cl. .......................... 260/293.67; 260/293.69; 260/293.75; 424/267
[58] Field of Search ...................... 260/293.67, 307 G

[56] References Cited

U.S. PATENT DOCUMENTS

| | | | |
|---|---|---|---|
| 3,917,615 | 11/1975 | Adelstein | 260/293.54 |
| 4,003,904 | 1/1977 | Adelstein | 260/293.54 |

OTHER PUBLICATIONS

*Chemical Abstracts,* vol. 71, Abstract No. 112937h (1969) [British Patent No. 1,161,801].
*Chemical Abstracts,* vol. 75, Abstract No. 20309j (1971) [Rips, R. et al., *Chim. Ther.* 1971, 6(1), 45–47].

*Primary Examiner*—Henry R. Jiles
*Assistant Examiner*—Richard A. Schwartz
*Attorney, Agent, or Firm*—Joy A. Serauskas

[57] ABSTRACT

This invention encompasses novel 5-[1,1-diphenyl-3-(4-phenylpiperidino)propyl]-2-methyl-1,3,4-oxadiazoles and structurally related compounds. These compounds are useful anti-diarrheal agents which, in addition to their anti-diarrheal utility, possess a utility as potent analgesic agents.

3 Claims, No Drawings

5-(1,1-DIPHENYL-3-(4-PHENYLPIPERIDINO)-PROPYL)-2-METHYL-1,3,4-OXADIAZOLE AND RELATED COMPOUNDS

The present invention addresses itself to 5-[1,1-diphenyl-3-(4-phenylpiperidino)propyl]-2-methyl-1,3,4-oxadiazole and related compounds thereof. Specifically, this invention addresses itself to compounds of the general formula (I)

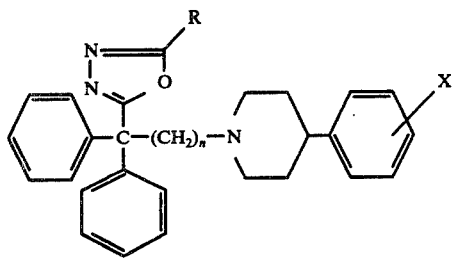

wherein R is an alkyl radical containing from 1 to 4 carbon atoms, X is hydrogen, halo or an alkyl radical containing from 1 to 4 carbon atoms and n is a positive integer from 1 to 3.

The alkyl radicals are exemplified by methyl, ethyl, propyl, butyl and the corresponding branched-chain isomers thereof. The term halo is exemplified by chloro, fluoro, bromo, and iodo.

A particularly preferred embodiment of this invention is that of formula (I) wherein R is methyl, X is hydrogen and n is 2.

Equivalent to the compounds of formula (I) for the purposes of the invention are the pharmaceutically acceptable acid addition salts thereof. Such acid addition salts can be derived from a variety of inorganic and organic acids such as sulfuric, phosphoric, hydrochloric, hydrobromic, hydroiodic, sulfamic, citric, lactic, pyruvic, oxalic, maleic, succinic, tartaric, cinnamic, acetic, benzoic, salicylic, gluconic, ascorbic and related acids.

Compounds of the instant invention are prepared as set out in the following Scheme A.

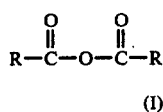

(I)

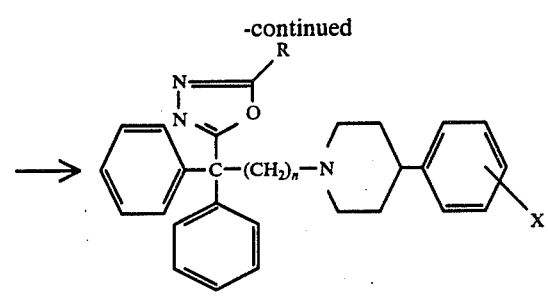

SCHEME A

The nitrile precursors of the present invention are prepared by reacting an amine of the formula

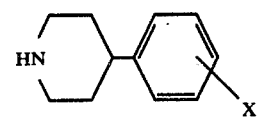

wherein X is hydrogen, halo or an alkyl radical containing from 1 to 4 carbon atoms with a halide of the formula

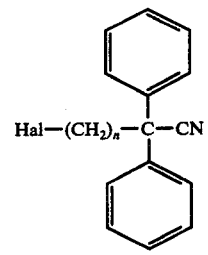

wherein Hal is chlorine or bromine and n is a positive integer from 1 to 3.

Alternately the nitriles can be prepared from a procedure which is described in U.S. Pat. No. 3,299,044 and includes the reaction of diphenylacetonitrile of the formula

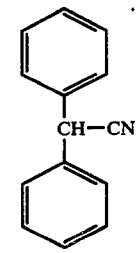

first with sodamide and then with an alkyl halide of the formula

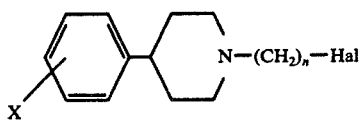

wherein Hal, X and n are defined as before.

As is shown in Scheme A, treatment of the nitrile with azide ion by methods similar to those described by G. Moersch and D. Morrow, J. Med. Chem., 10, 149

(1967) provides the corresponding tetrazole. The tetrazole intermediates are then converted to the corresponding 1,3,4-oxadiazole by treatment with an appropriate acid anhydride following the procedures substantially as described by R. Huisgen et al., *Chem. Ber.*, 93, 2106 (1960).

For instance 2.0 parts of 5-[1,1-diphenyl-3-(4-phenylpiperidino)propyl]tetrazole, 4.8 parts of acetic anhydride and 20 parts by volume of pyridine were heated at reflux for a period of 1 hour and 20 minutes. After the reaction period is completed, the reaction mixture is cooled and then stripped in vacuum to leave a residue. This residue is taken up in ether. The ether solution is washed with sodium hydroxide, dried over sodium sulfate and then stripped in vacuum to leave a gum which is 5-[1,1-diphenyl-3-(4-phenylpiperidino)propyl]-2-methyl-1,3,4-oxadiazole.

The compounds of the present invention are useful in consequence of their valuable pharmacological properties. They are, for example, potent anti-diarrheal agents as evidenced by their ability to inhibit gastrointestinal motility as set out in the following test.

Charcoal Meal Test

The method used for this assay is a modification of the techniques previously described by Macht and Barba-Gose, *J. Amer. Pharm. Ass.*, 20, 558 (1931), and Janssen and Jageneau, *J. Pharm. Pharmacol.*, 9, 381 (1957). Details are as follows:

A group of six, male Charles River mice weighing 20–25 g. which have been previously fasted for 24 hours are pretreated with the test compounds administered orally as a solution in water or suspended in 0.5% methyl cellulose. A constant volume of 10 ml./kg. is employed. Thirty minutes following administration of the test compounds, the animals are given a single oral dose of charcoal which consists of 0.2 ml. per mouse of 10% charcoal suspended in 1.0% methyl cellulose. Three and a half hours after charcoal administration, the animals are sacrificed and the cecum examined for the absence or presence of charcoal on an all-or-none basis.

The median effective dose ($ED_{50}$) is then calculated for each compound using the logistic method of Berkson (1953).

A representative compound of this invention which is active in the Charcoal Meal Test is 5-[1,1-diphenyl-3-(4-phenylpiperidino)propyl]-2-methyl-1,3,4-oxadiazole; this compound has a median effective does ($ED_{50}$) of 0.91 ± 0.34 mg./kg., IG in the Charcoal Meal Test. Anti-diarrheal agents which are described in Goodman and Gilman, *The Pharmacological Basis of Therapeutics*, Collier-Macmillan, London (1970) p. 258 are active in this test.

In addition to their anti-diarrheal activity, the compounds of this invention demonstrate analgesic activity. The assessment of this activity is conducted by the following tests.

Tail Clip Test

A special clip is applied to the base of the tail of the mouse and the time for the animal to turn around to bite at it is measured. The sensitivity of each mouse is determined ½ hour prior to drug administration. Only those mice attempting to bite the clip are included in the experiment. The test compound is then administered and the response to placement of the clip is determined at 30, 60, 90 and 120 minutes after treatment. A response is considered positive if the animal takes more than 2 times the pre-drug time to bite at the clip at any of these time intervals. A test compound is considered active when 50 percent or more of the animals used show a positive response.

Mouse Hot Plate Test

A mouse is placed in a restraining cylinder on a hot plate with the temperature controlled at 55° ± 0.3° C. The reaction time of the mouse to lick a foot or jump is measured at 60, 40, and 20 minutes before, and 30, 60, 90 and 120 minutes after administration of the test compound. The "normal" reaction time is measured as the median of the three pretreatment reaction times. A positive response consists of a reaction time greater than twice the normal time at any of the post-treatment times. A dose of test compound is considered active when 50 percent or more of the animals used show a positive response.

A representative compound of this invention which is active in both the Tail Clip Test and the Mouse Hot Plate Test is 5-[1,1-diphenyl-3-(4-phenylpiperidino)-propyl]-2-methyl-1,3,4-oxadiazole; this compound has a median effective dose ($ED_{50}$) of 4 mg./kg., IG in the Mouse Hot Plate Test and 2 mg./kg., IG in the Tail Clip Test.

The compounds of formula (I) may be combined with various pharmaceutical carriers to provide compositions suitable for use in the treatment of diarrhea. The dosage of these compounds is dependent upon various factors, such as the compound employed and the particular response obtained. Typical dosages for use as an anti-diarrheal agent vary from 0.1 to 25 mg./kg. per day administered orally.

The following examples described in detail the preparation of compounds of the present invention. It will be apparent to those skilled in the art that many modifications both of materials and method, may be practiced without departing from the purpose and intent of this disclosure. Throughout the examples hereinafter set forth, temperatures are given in ° C. and relative amounts in parts by weight, except as otherwise noted.

EXAMPLE 1

A mixture of 18.6 parts of 2,2-diphenyl-4-bromobutyronitrile, 10.0 parts of 4-phenylpiperidine, 8.0 parts of N,N-diisopropylethylamine and 200 parts by volume of 2-methoxyethanol is heated at reflux for 16 hours. The solution is then cooled and stripped in vacuum. The resulting residue is partitioned between dilute sodium hydroxide and ether. Extraction of the ether phase with dilute hydrochloric acid results in the precipitation of an oil. This oil and the aqueous phase of the partitioning are combined, treated with aqueous sodium hydroxide and extracted with 1:1 ether-benzene mixture. The ether-benzene extract is dried over sodium sulfate and stripped in vacuum to give a solid. Crystallization of the solid from a mixture of skelly B and ether provided 2,2-diphenyl-4-(4-phenylpiperidino)butyronitrile, melting at 88° – 89.5° C. and having the following formula

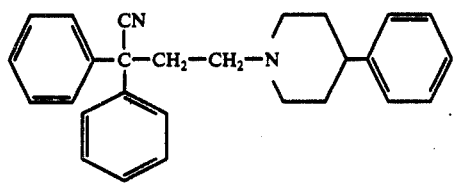

11.0 Parts of 2,2-diphenyl-4-(4-phenylpiperidino)-butyronitrile are dissolved in 55 parts by volume of dimethylformamide along with 2.82 parts of sodium azide, 2.32 parts of ammonium chloride and 0.04 parts of lithium chloride. This mixture is heated under a nitrogen atmosphere, in an oil bath which is kept at 125° C. The solution is cooled and poured into water which caused the formation of a gummy precipitate. The solvent phase is decanted from the gum. The gum is then crystallized from a mixture of methanol-ether and dried in vacuum to provide an off-white solid which is recrystallized from a mixture of methanol-ether and again dried in vacuum to provide 5-[1,1-diphenyl-3-(4-phenylpiperidino)propyl]-1H-tetrazole hemimethanolate, melting at 149° – 157° C. and having the following formula

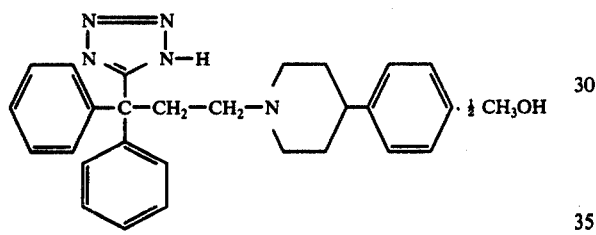

2.0 Parts of 5-[1,1-diphenyl-3-(4-phenylpiperidino)-propyl]-1H-tetrazole hemimethanolate, 6.21 parts of acetic anhydride and 20 parts by volume of pyridine are heated together to reflux for 1 hour and 20 minutes. The mixture is then cooled and stripped in vacuum. The resulting residue is taken up in ether. The ether solution is washed with sodium hydroxide, dried over sodium sulfate and then stripped in vacuum to give a gum. 1.74 Parts of this gum dissolved in 6 parts by volume of methanol and 0.35 part of oxalic acid dissolved in 4 parts by volume of methanol are mixed together. This solution is diluted with ether to just below the point of cloudiness. The crystals which form are filtered off and dried in vacuum to provide 5-[1,1-diphenyl-3-(4-phenyl-piperidino)propyl]-2-methyl-1,3,4-oxadiazole oxalate, melting at 180° – 190° C., having the following formula

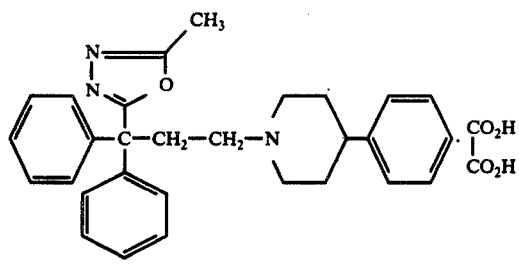

EXAMPLE 2

Substitution of an equivalent quantity of 2,2-diphenyl-3-bromopropionitrile for the 2,2-diphenyl-4-bromobutyronitrile of Example 1 and repetition thereof of the procedure which is described in Example 1 affords 5-[1,1-diphenyl-2-(4-phenylpiperidino)ethyl]-2-methyl-1,3,4-oxadiazole and has the following formula

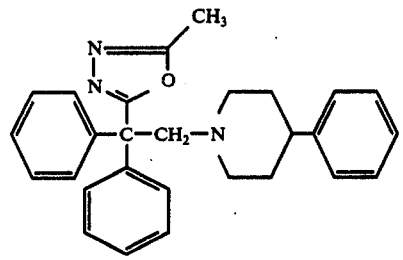

EXAMPLE 3

Repetition of the procedure detailed in Example 1 using an equivalent quantity of 4-(4-chlorophenyl)-piperidine for the 4-phenylpiperidine affords 5-{1,1-diphenyl-3-[4-(4-chlorophenyl)piperidine]propyl}-2-methyl-1,3,4-oxadiazole and has the following formula

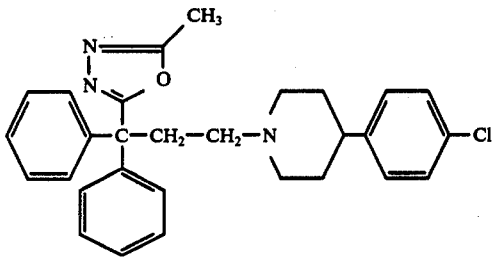

What I claim is:
1. A compound of the general formula

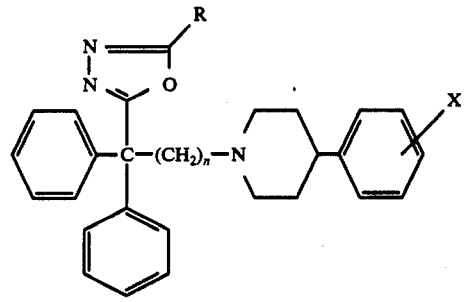

wherein R is an alkyl radical containing from 1 to 4 carbon atoms, X is hydrogen, halo or an alkyl radical containing from 1 to 4 carbon atoms and $n$ is a positive integer from 1 to 3.
2. A compound according to claim 1 which is 5-[1,1-diphenyl-3-(4-phenylpiperidino)propyl]-2-methyl-1,3,4-oxadiazole.
3. A compound which is 5-[1,1-diphenyl-3(4-phenyl-piperidino)propyl]-2-methyl-1,3,4-oxadiazole oxalate.

* * * * *